United States Patent [19]

Kesling

[11] 4,180,912

[45] Jan. 1, 1980

[54] ORTHODONTIC LIGHT WIRE APPLIANCE

[76] Inventor: Peter C. Kesling, Green Acres, LaPorte, Ind. 46350

[21] Appl. No.: 944,742

[22] Filed: Sep. 22, 1978

[51] Int. Cl.² .............................................. A61C 7/00
[52] U.S. Cl. ........................................ 433/13; 433/14
[58] Field of Search ......................................... 32/14 A

[56] References Cited

U.S. PATENT DOCUMENTS

| 2,686,365 | 8/1954 | Schurter | 32/14 A |
|---|---|---|---|
| 3,237,305 | 3/1966 | Hegedus | 32/14 A |
| 3,391,461 | 7/1968 | Johnson | 32/14 A |
| 3,686,758 | 8/1972 | Kesling | 32/14 A |
| 3,772,787 | 11/1973 | Hanson | 32/14 A |
| 3,838,514 | 10/1974 | Poluk | 32/14 A |
| 4,023,274 | 5/1977 | Wallshein | 32/14 A |

OTHER PUBLICATIONS

Publication–Lancer Pacific ad, Enamelkote, Jul. 1978, Journal of Clinical Orthodontics.

Primary Examiner—Robert Peshock
Attorney, Agent, or Firm—Lloyd L. Zickert

[57] ABSTRACT

An orthodontic appliance for covering the outer surfaces of a light wire bracket and/or for securing an archwire thereto, which includes a body of tooth colored plastic material having means for detachably securing the appliance to a bracket, and being structured to substantially cover the faces of the bracket so that none are visible from the labial side.

18 Claims, 24 Drawing Figures

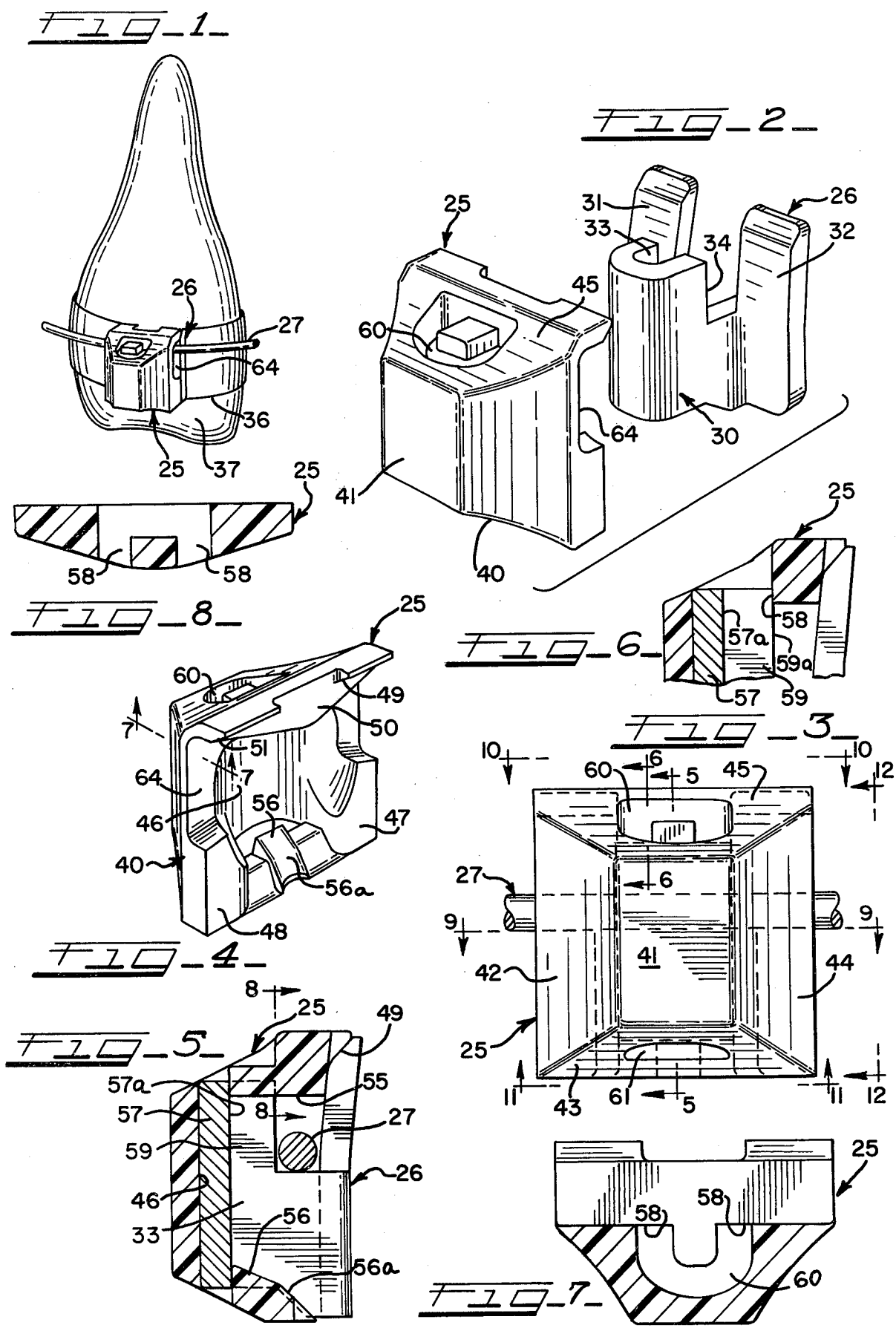

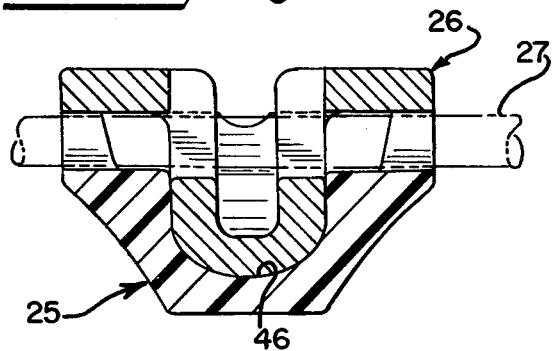
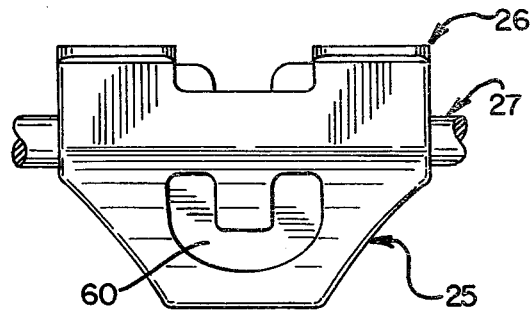
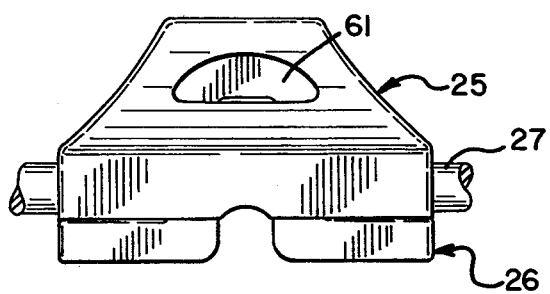
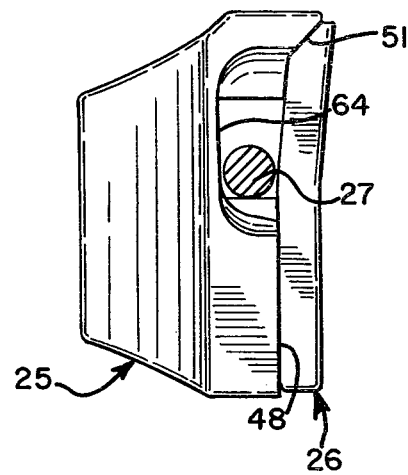
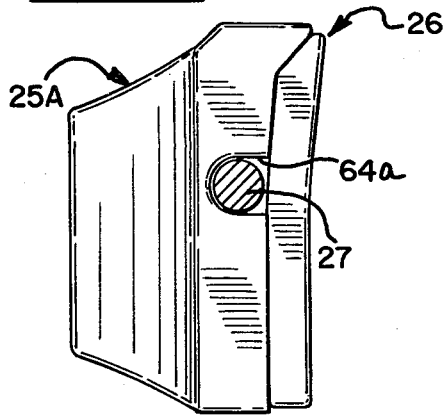
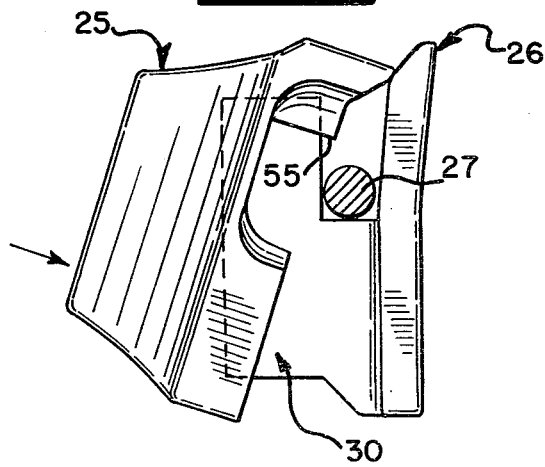

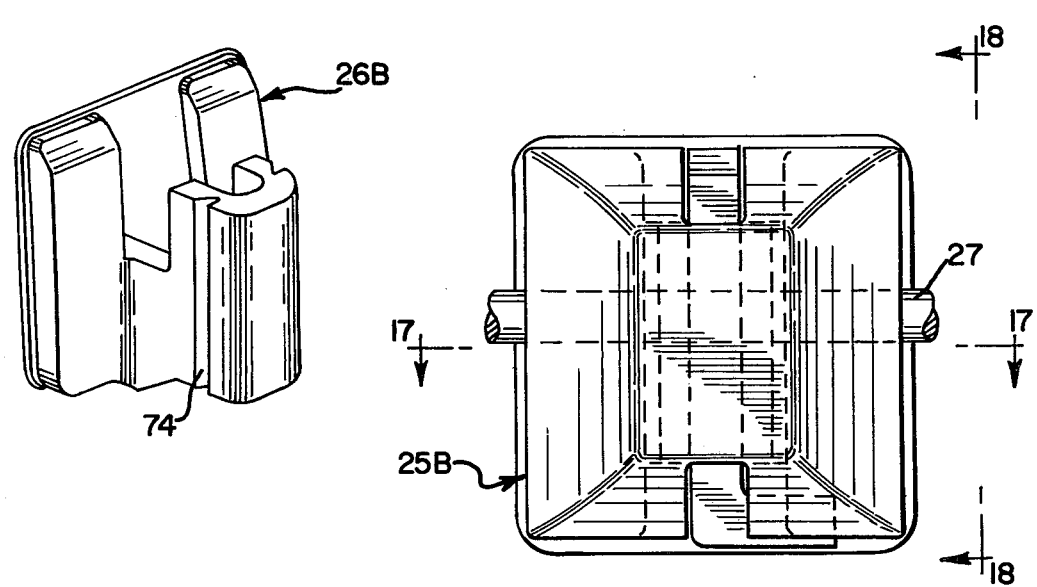
FIG_15_
FIG_16_
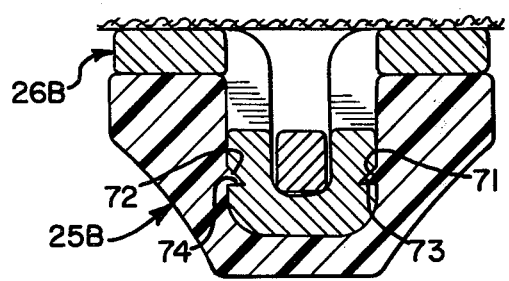
FIG_17_
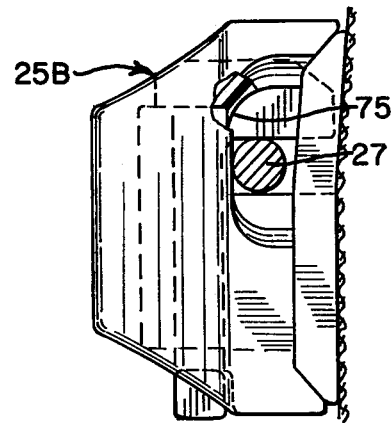
FIG_18_

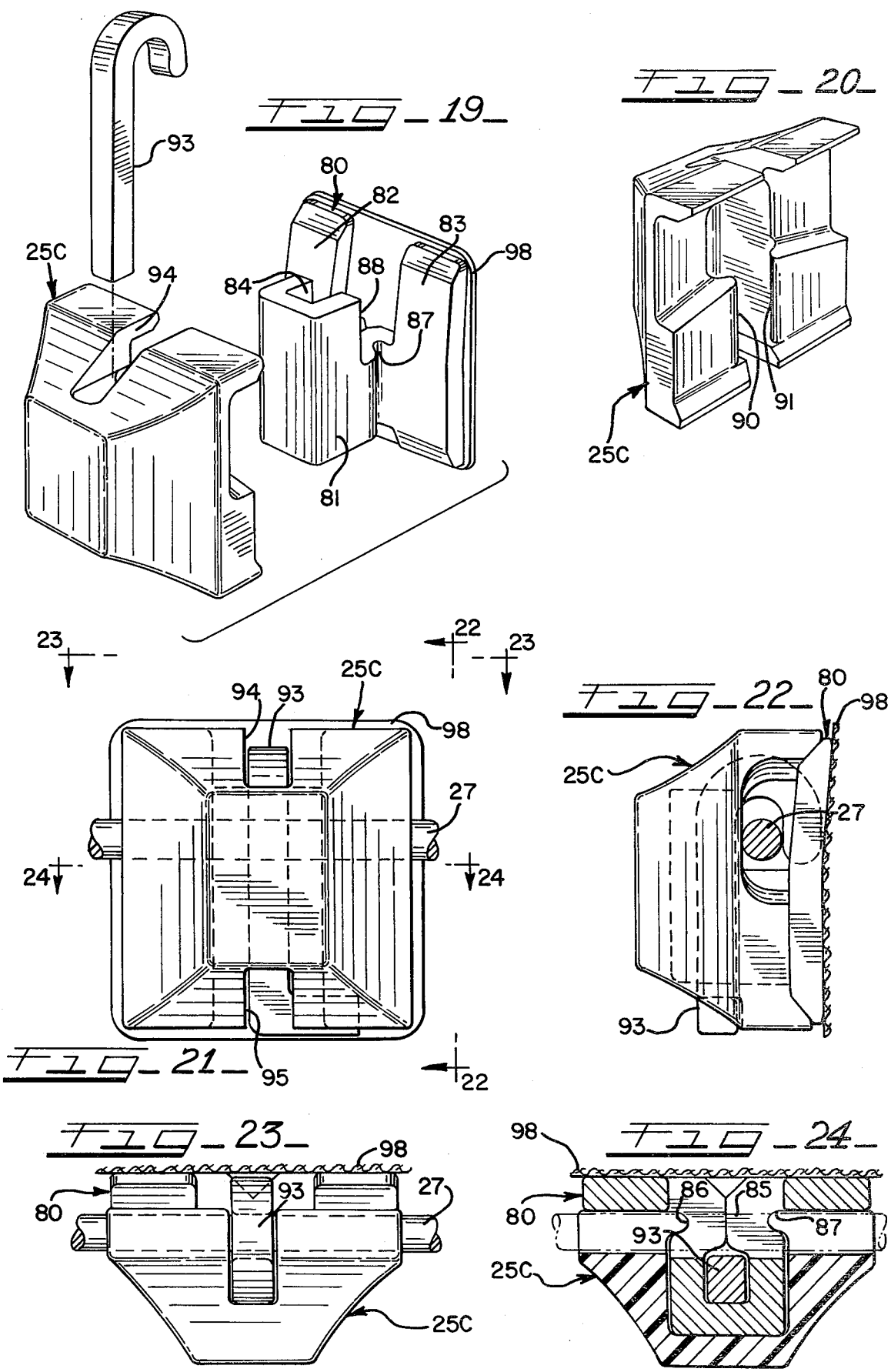

ORTHODONTIC LIGHT WIRE APPLIANCE

This invention relates in general to an orthodontic appliance, and more particularly to an appliance used in combination with a light wire bracket for particularly hiding metal surfaces of the bracket and/or for securing an archwire in place on the bracket.

Heretofore, it has been well known to secure archwires to metal light wire brackets by use of lock pins, such as shown in U.S. Pat. No. 3,085,336. It has also been known to secure archwires to metal light wire brackets by use of lock rings, such as shown in U.S. Pat. No. 3,686,758. Further, there have been efforts to minimize the noticeability of a patient being treated by orthodontic appliances which have included the development of clear and tooth colored plastic brackets together with development of adhesives for attaching the brackets to teeth. Generally, these appliances have been applied to the anterior teeth which are the most visible when a person wearing the appliances smiles. However, the plastic brackets do not have the strength of metal brackets, whereby the plastic brackets often fail during usage, and accordingly, it sometimes becomes necessary to remove a damaged or worn plastic bracket prior to completion of treatment and replace it with another. Such is time-consuming and costly. It has also been known to apply a colored coating of material directly to a metal bracket for the purpose of improving aesthetics, but such a coating is subject to chipping and peeling during normal usage in the patient's mouth, which results in an undesirable appearance, and the coating process utilizes heat which softens the metal and impairs the ability of the bracket to withstand forces without affecting its dimensional integrity.

Metal brackets most often have been secured to a band which in turn is cemented to a tooth. Metal pads have been recently developed onto which a metal bracket may be secured and which then in turn can be adhesively secured to a tooth, and which overcomes the problems of breakage and worn plastic brackets. However, the surfaces of the metal bracket are visible from the labial side, and while the elimination of bands somewhat lessens the noticeability of appliances being worn on teeth, the brackets are readily visible.

The present invention overcomes the problem of noticeability of a metal bracket by nearly completely hiding the surfaces of the bracket that normally would be visible from the labial. More specifically, the appliance of the present invention includes a body of tooth colored plastic material that is structured for mounting onto a metal bracket and which includes means for engaging and detachably securing the appliance to the metal bracket, together with optional means for coacting with the archwire slot of the bracket to capture an archwire in the slot. Further, the body of the appliance is structured in size to essentially completely cover the surfaces of the metal bracket that would normally be visible from a generally labial direction. Accordingly, the appliance of the invention, while sometimes serving to lock the archwire in the archwire slot of the bracket, serves to hide the bracket, thereby making it more aesthetically appealing and minimizing the noticeability of the bracket as worn on the tooth of a patient. The appliance of the invention may be easily snapped into place on a bracket since the plastic material has a sufficient flex to allow movement of detent portions out of normal position for attachment to the bracket and back to a normal position for securing the appliances to the bracket. Further, the appliance of the invention may be disposed of and replaced with another at the various stages of treatment of a patient to thereby provide the highest degree of reliability of retention of the archwire on the bracket between visits to the orthodontist.

It may be appreciated that the appliance illustrated in the above-mentioned U.S. Pat. No. 3,686,758, which may be deemed a lock ring and which serves to lock an archwire in place on a light wire bracket, whether it is made of metal or a plastic material, would not cover all the surfaces of the bracket which would be visible from the labial. It is this disadvantage that the present invention overcomes, and the present invention therefore is an improvement over the structure in that patent.

It is therefore an object of the present invention to provide a new and improved appliance for a metal light wire bracket which functions to hide the bracket to aesthetically improve the appearance of the patient wearing the bracket and/or for retaining an archwire in place.

Another object of the invention is to provide an appliance for a metal light wire bracket which will generally cover the bracket and retain an archwire in place, and which may also reduce the labiolingual width of the bracket archwire slot to accommodate wire having a labiolingual dimension smaller than the slot.

A further object of this invention is in the provision of a molded plastic appliance that may be inexpensively manufactured for use in retaining an archwire on a metal light wire bracket and for substantially completely hiding the surfaces of the bracket visible from the labial so as to aesthetically improve the appearance of a patient having appliances for orthodontic treatment and minimizing noticeability of the appliances.

Another object is to provide a means of positively controlling the tipping movements of a tooth in any direction about an archwire having a round or flat-sided cross section.

Other objects, features and advantages of the invention will be apparent from the following detailed disclosure, taken in conjunction with the accompanying sheets of drawings, wherein like reference numerals refer to like parts, in which:

FIG. 1 is a perspective view of a tooth having a bracket mounted thereon wherein the bracket is mounted on a band shown in phantom and illustrating the appliance of the present invention as it is mounted in place on the bracket for retaining the archwire in the bracket archwire slot and for substantially hiding the surfaces of the bracket that would be visible to the labial;

FIG. 2 is an enlarged perspective view of a metal light wire bracket and the plastic appliance of the present invention and illustrating the two elements in exploded fashion;

FIG. 3 is a front elevational view of the appliance of the present invention as it is mounted onto a light wire bracket and for retaining an archwire in place and illustrating the bracket partially in dotted line;

FIG. 4 is a rear or lingual perspective view of the appliance of the present invention;

FIG. 5 is a vertical sectional view taken through the appliance and bracket in FIG. 3 and taken substantially along line 5—5 of FIG. 3;

FIG. 6 is a fragmentary detailed sectional view taken substantially along line 6—6 of FIG. 3;

FIG. 7 is a transverse sectional view taken substantially along line 7—7 of FIG. 4 and looking in the direction of the arrows;

FIG. 8 is a detailed vertical sectional view taken substantially along line 8—8 of FIG. 5;

FIG. 9 is a transverse sectional view taken through the appliance and bracket of FIG. 3 and substantially along line 6—6 of FIG. 3;

FIG. 10 is a top plan view of the appliance and bracket of FIG. 3 and taken substantially along line 10—10 of FIG. 3;

FIG. 11 is a bottom plan view of the bracket and appliance of FIG. 3 and taken substantially along line 11—11 of FIG. 3;

FIG. 12 is an end elevational view of the appliance and bracket of FIG. 3 and taken substantially along line 12—12 of FIG. 3;

FIG. 13 is an end elevational view of a bracket and appliance of the invention and illustrating the manner in which the appliance is mounted onto the bracket;

FIG. 14 is an end elevational view of the bracket and appliance of the invention which is modified by having a narrower archwire receiving slot to prevent tipping movement between the wire and the bracket;

FIG. 15 is a perspective view of a metal light wire bracket modified to receive a still further modified appliance according to the present invention;

FIG. 16 is a front elevational view similar to that of FIG. 3 of the bracket of FIG. 15 together with a modified appliance and a lock pin therein;

FIG. 17 is a transverse sectional view taken through the assembly of FIG. 16 and substantially along line 17—17 thereof;

FIG. 18 is a side elevational view of the assembly of FIG. 16 which shows additional retention means for retaining the appliance in place on the bracket;

FIG. 19 is an exploded view of a modified light wire bracket and a modified appliance according to the invention together with an archwire lock pin for illustrating a modification of the invention applicable to a light wire bracket of another construction;

FIG. 20 is a rear or lingual perspective view of the appliance shown in FIG. 19;

FIG. 21 is a front elevational view of the appliance, bracket and lock pin shown in FIG. 19 in assembled relation, together with dotted lines showing the relationship between the bracket and the appliance;

FIG. 22 is an end elevational view of the assembly of FIG. 21 taken substantially along line 22—22 of FIG. 21;

FIG. 23 is a top plan view of the assembly of FIG. 21 taken substantially along line 23—23 of FIG. 21; and FIG. 24 is a transverse sectional view taken through the assembly of FIG. 21 and taken substantially along line 24—24 of FIG. 21.

The appliance of the invention is for use in combination with a metal bracket of the light wire type although both round light wire and heavy flat sided cross sectional wire may be used with such a bracket. A flat-sided wire may be of any polygonal shape, and may be of the well known edgewise type. Exemplary of the type of bracket that may be used in combination with the appliance is the one illustrated in FIGS. 2, 3 and 5 to 11, which is a model TP 256 bracket made by TP Laboratories, Inc. of LaPorte, Ind. illustrated generally in U.S. Pat. No. 3,178,821, and the bracket shown in FIGS. 19 and 21 to 24, which is of a type illustrated in U.S. Pat. No. 3,408,739. However, it may be used in combination with light wire brackets of other constructions not illustrated in this application as the object of the present invention is to substantially completely hide the surfaces of a bracket that might be visible from the labial and/or to retain an archwire on the bracket. While the appliance of the invention will be described as being used principally with a metal light wire bracket, it should be appreciated that it could be used with a plastic light wire bracket if so desired, although there would generally not be the need to hide the surfaces of a plastic bracket as there is with respect to a metal bracket.

It should be appreciated that the appliance of the invention may be used in combination with a bracket that is secured to a tooth by way of being secured to a band that is thereafter cemented to a tooth, as shown in FIG. 1, or with a bracket that is first secured to a metal pad that is in turn adhesively secured to the surface of a tooth, as shown in FIG. 19. In either case the appliance of the present invention is intended to essentially cover the bracket while securing an archwire to the bracket to hide the surfaces of the bracket visible from the labial or buccal side. In this respect, it should be appreciated that the appliance would be molded of a colored plastic material and if tooth colored would be of the same color as the surrounding teeth and not easily noticeable. Yet, other colors could be used if desired. The usual metal bracket is made of stainless steel and in any event would have a shiny or polished surface. By molding the appliance of the invention from a suitable tooth colored or otherwise opaque plastic material, the polished surface of the bracket would not be seen when the appliance is mounted on the bracket.

In the embodiment illustrated in FIGS. 1 to 13, the appliance of the invention is generally designated by the numeral 25 and sized to be used in combination with a metal light wire bracket 26 and which can serve to secure an archwire 27 to the bracket.

The bracket 26 includes a body 30 projecting labially from a pair of attaching or mounting flanges 31 and 32. The flanges 31 and 32 are sometimes referred to as welding flanges where welds are provided along the flanges to secure the bracket to a band or a pad. The flanges 31 and 32 also extend mesially and distally from the body 30. An occlusogingival opening 33 is defined by the body which is also notched at the gingival-lingual corner to define an archwire slot 34. The opening 33 usually receives a lock pin but may also receive other auxiliaries used in connection with orthodontic treatment. The archwire slot 34 extends mesiodistally of the bracket and opens upwardly or gingivally, and therefore upon placement of an archwire in the slot, it is necessary to provide a device for preventing the accidental escape of the archwire from the slot during the treatment process. In this respect, a lock pin or other device may be used. A lock ring such as shown in U.S. Pat. No. 3,686,758 could also be used.

Another form of light wire bracket is illustrated in FIGS. 19, 21 to 24, and still other forms of light wire brackets are commercially available, but in each bracket the elements above described in connection with the bracket 26 are usually present. Further, it is contemplated that the appliance of the present invention may be used on any light wire bracket although some slight modifications may be needed to adapt it for specific use on a specific bracket. Yet, in each instance the appliance would serve in the same fashion, i.e., to cover the surfaces of the bracket so they are not visible from the labial side and/or to retain the archwire in the archwire slot of the bracket.

It will be appreciated the bracket may be mounted to a tooth in any suitable fashion, and the bracket 26 is illustrated in FIG. 1 as being mounted to a tooth band 36 which in turn is cemented to the tooth 37. However, as illustrated in connection with the embodiment of FIGS. 19 to 24, the bracket may be mounted onto a pad or base which is in turn suitably adhesively secured to the outer surface of a tooth.

The appliance 25 is molded from a suitable plastic which could be opaque and colored to match the color of a tooth or otherwise colored if desired. Materials that would be satisfactory include polyethylene and Lexan. The material should have a sufficient resiliency so that portions can flex during mounting and demounting of the appliance onto a bracket.

The appliance 25 includes a body 40 structured to fit over the bracket body 30 and against the body and the attaching flanges 31 and 32. The body is somewhat rectangular or square in outer configuration as viewed from the labial, as seen particularly in FIG. 3, and is formed to include an outermost flat surface 41 and from the edges thereof inwardly sloping surfaces 42, 43, 44 and 45.

Looking at the lingual side of the appliance body 40, a cavity is defined having a wall or surface 46 that mates with the outer surface of the bracket body 30 when the appliance is mounted on the bracket 26, as seen in FIGS. 5 and 6. Bearing surfaces 47 and 48 are formed at the lingual side of the appliance body 40 and at the occlusal end for engaging against the attaching flanges of the bracket. At the gingival end of the appliance body and also on the lingual side are bearing surfaces 49 and 51 which also engage the labial surface of the attaching flanges of the bracket, as seen most clearly in FIGS. 5 and 9.

The appliance is held in place on the bracket by means of inwardly extending detent portions which include a gingival detent portion 55 and an occlusal detent portion 56. These detent portions enter into the upper and lower or gingival and occlusal ends of the bracket body opening 33 and engage the lingual surface 57a of the labial wall 57 of the bracket body 30 at the gingival and occlusal ends of the wall. In this respect, the upper and lower ends 33, as defined by the bracket body, function as sockets for receiving the detent portions, and therefore it is possible to utilize the appliance of the invention with a bracket having only sockets and not an opening through the body. The manner in which the detent portions 55 and 56 engage with respect to the bracket and particularly the opening 33 are shown in FIG. 5.

The appliance is also retained on the bracket by shoulders 58 located at opposite sides of the gingival detent 55, which shoulders lock against the lingual surfaces 59a of the mesial and distal walls 59 of the bracket body, as seen in FIG. 6. Further, it can be appreciated the shoulders provide retention at the gingival end of the appliance where the gingival indent 55 may be eliminated to permit access to the bracket opening 33 for utilizing auxiliaries, such as to permit the insertion of legs of uprighting springs and torqueing auxiliaries. The gingival indent could be removed by the manufacturer or by the orthodontist.

The appliance 25 is mounted onto the bracket by applying the appliance from the labial side of the bracket. The appliance may be pushed onto the bracket and essentially snapped into place, wherein the detent portions extend into the opening of the bracket body and engage the lingual surface of the labial wall 57 and the shoulders 58 engage the lingual surfaces 59a of the mesial and distal walls 59. One efficient manner of mounting the appliance to the bracket is somewhat illustrated in FIG. 13, wherein the appliance is essentially hung onto the upper end of the bracket so that the detent portion 55 registers with the opening 33 of the bracket body and a force is applied to the outer or labial lower end of the appliance to cam the occlusal detent portion 56 over the occlusal end of the bracket body and into place. During the forcing of the appliance onto the bracket, it will be appreciated that the appliance will flex so that the detent portions will spread apart and allow the detent portions and the shoulders to ultimately engage the lingual surfaces of the bracket body. As seen in FIG. 5, a sloping or camming surface 56a is provided on the surface of the detent portion 56 which will engage the bracket as the appliance is forced into seated position. When the appliance reaches seated position, the detent portion 56 snaps into locked engagement with the bracket body 30. While the detent portions 55 and 56 are shown in opposed relation along the occlusogingival axis and for engaging into the bracket body opening 33, it should be appreciated that detent portions may be otherwise formed for locking to parts of the bracket and thereby detachably securing the appliance to the bracket. It will be appreciated that by cutting and/or forcing the appliance away from the bracket, it can be demounted therefrom when desired without disturbing the mounting of the bracket on the tooth.

In order to enhance the flexibility established between the detent portions 55 and 56, openings are provided in the body of the appliance. An upper opening 60 is provided in the upper sloping wall 45 of the appliance body in proximity to the upper detent portion 55, while an opening 61 is provided in the lower sloping surface 43 of the appliance body in the proximity of the lower detent portion 56. It should be appreciated that the appliance could be made without the openings providing the material has sufficient flexibility in order to enable mounting of the appliance onto a bracket.

A lingually opening mesiodistally extending slot 64 is provided at the lingual side of the appliance for registering with the archwire slot 34 of the bracket 26 to insure desired tooth movements. The appliance slot 64 has an occlusogingival depth substantially greater than the cross section of the round archwire 27 so that suitable tipping action can be obtained by the bracket and the archwire, thereby allowing tipping action of a tooth to be obtained. The labiolingual depth of the slot 64 would be substantially equal to the depth of the bracket archwire slot where the labiolingual depth of the wire would substantially equal the bracket depth. If it were desired the bracket slot be reduced, such could be accomplished with the appliance, where its slot width is reduced labiolingually. In the event closer control is needed between the archwire and the tooth and no tipping action is desired, the slot may be narrowed such as the slot 64a in the appliance 25A of FIG. 14, which does not allow any tipping action between the archwire 27 and the bracket 26. Other than the size and shape of the archwire slot in the appliance shown in the embodiment of FIG. 14, that appliance is otherwise structured similar to the appliance illustrated in FIGS. 1 to 13.

For even greater control and deliverance of forces to the teeth through the appliance, the archwire slot can be designed to snugly receive a flat-sided archwire. This would permit control of the angular position of the tooth in all directions.

Accordingly, it may be appreciated from the various views of the appliance 25 as it is mounted on a bracket and particularly the frontal or labial view of FIG. 3 that once the appliance is in mounted place on a bracket, it will cover or hide substantially all surfaces of the bracket which might be visible from the labial side. Therefore, when the appliance is made of a color to blend with the color of the teeth, the bracket will be camouflaged and the noticeability of appliances will be minimized.

A modified appliance 25B is illustrated in FIGS. 16 to 18 for use on a modified light wire bracket 26B shown in FIG. 21. As illustrated in FIG. 16, upper and lower detent portions like 55 and 56 of the appliance 25 have been omitted so that a lock pin 70 can be utilized with the appliance for obtaining additional retention of the archwire 27. In order to utilize a lock pin or similar type of auxiliary which is inserted into the opening 33 of the bracket, it is necessary to have the upper and lower ends of the appliance open. In this event, the means for detachably securing the appliance to the bracket must take a different form from that illustrated in the embodiment of FIGS. 1 to 13.

The body of the appliance 25B is provided with inwardly projecting detents extending occlusogingivally and indicated in FIG. 17 by the numerals 71 and 72 for engagement into the occlusogingivally extending indents 73 and 74 formed on the outer surfaces of the bracket body and particularly along the mesial and distal surfaces of the body. When the appliance 25B is mounted onto the bracket, the detents 71 and 72 spread apart and ultimately snap back together to engage into the indents 73 and 74. In order to additionally provide retention of this embodiment when the appliance is applied to a bracket, additional lugs or detents 75 may be formed at the upper and/or lower ends of the appliance for engaging the gingival and/or incisal lingual corners of the bracket and on the surfaces which face lingually. This arrangement is like the shoulders 58 in the embodiment of FIGS. 1 to 8.

Accordingly, the appliance of embodiment 25B comprehends a modification of a bracket which requires indentations to be placed along the opposite sides of the bracket body. Otherwise, it can be appreciated that the appliance 25B will serve the same purpose as the embodiment of FIGS. 1 to 13 in that it will cover the surfaces of the bracket facing labially, also lock the archwire in place on the bracket, and provide the degree of tooth control desired.

Another embodiment of the invention is shown in FIGS. 19 to 24, wherein the appliance, generally designated by the numeral 25C, differs from the appliances 25, 25A and 25B in that the means for engaging the bracket is structured for fitting with a bracket of the type shown in the aforementioned U.S. Pat. No. 3,408,739. The bracket in FIGS. 19 and 21 to 24 is generally designated by the numeral 80 and includes a body 81 projecting labially from attaching flanges 82, 83 and wherein the body 81 defines an occlusogingivally extending opening 84 in slightly spaced relation from the mounting flanges 82 and 83. The opening 84, as seen particularly in FIG. 24, is closed on four sides at the lower end of the body and open on the lingual side at the upper end of the body. A bridging or connecting portion 85 extends between the body and the attaching flanges and defines an edge against which an archwire may engage. The bridging or connecting portion 85 is formed with respect to the body 81 and defines opposed occlusogingivally extending indents 86 and 87 adjacent to the attaching flanges 82 and 83. The archwire slot 88 formed in the gingival-lingual corner of the body is open at the gingival end like the archwire slot of the bracket shown in the previous embodiments.

Because of the ready-made indents 86 and 87 in the bracket 80, mating detent portions 90 and 91 formed on the lingual side of the body of the appliance 25C provide the necessary structure for allowing detachable securement of the appliance 25C to the bracket 80. This also allows the upper and lower ends of the appliance to be open so that a lock pin 93 of any desired type may also be mounted on the bracket to provide additional retention of the archwire 27. Accordingly, openings 94 and 95 are provided in the appliance to facilitate the mounting of a lock pin on the bracket and to open up the occlusogingivally extending body opening 84. It can be appreciated that the lingual side of the appliance 25C includes a cavity shaped to mate with the body of the bracket seen particularly in FIG. 21 and also that the appliance will otherwise function in the same manner as the appliance in the previous embodiments and that it can be detachably secured to the bracket for the purpose of retaining the archwire in the bracket archwire slot and/or for the purposes of covering the surfaces of the bracket which would be visible from the labial and to provide desired tooth movements by altering the design of the lingual face of the appliance that coacts with the arch wire. Because the appliance embodiments in FIGS. 15 to 18 and 19 to 24 are open at the gingival and occlusal ends in alignment with the pin openings of the brackets, uprighting springs and other torqueing auxiliaries can easily be used with these appliances.

It is further illustrated in FIGS. 19 and 21 to 24 that a light wire bracket may be mounted onto a pad 98 which is suitable for directly bonding the appliance to the outer surface of a tooth. It will be appreciated that the brackets of the previous embodiments could likewise be first mounted onto a pad which would be then directly adhesively bonded to a tooth.

Further, the appliance 25C would be molded in the same fashion as the appliances of the previous embodiments in that it would be molded of a suitable material that would be tooth colored and would have the desired resiliency for flexing purposes so that the appliance can be easily mounted onto a bracket and thereafter demounted when desired.

While the appliance embodiments illustrated include means for retaining the archwire on a bracket, it may be appreciated the appliance may be structured for only hiding the labial surfaces of a bracket where the archwire would otherwise be secured to the bracket. Thus, soiled or otherwise damaged appliances could be replaced without affecting the attachment of the archwire.

From the foregoing, it will be appreciated that the appliance of the present invention is especially useful for aesthetically improving the visual appearance of a person wearing appliances on the anterior teeth as the noticeability of the appliances will be minimized by the present invention.

It will be understood that modifications and variations may be effected without departing from the scope of the novel concepts of the present invention, but it is understood that this application is to be limited only by the scope of the appended claims.

The invention is hereby claimed as follows:

1. An orthodontic appliance for use in combination with a metal bracket having a body with an occlusogingivally extending opening, attaching flanges at the lingual side of the body, and a mesiodistally extending archwire slot opening gingivally at the gingivolingual corner of the body, said appliance comprising a body of plastic material capable of flexing for mounting same on a bracket, said body having means coacting with the bracket body for detachably securing the appliance to the bracket and means coacting with the archwire slot to retain an archwire therein, and said body having means to cover the labial surfaces of the bracket body and flanges and the mesial and distal surfaces of the bracket body so that substantially all of said surfaces are not visible from the labial.

2. The appliance defined in claim 1, wherein said appliance body means for detachably securing the appliance to the bracket includes detent means at the occlusal and gingival ends of the appliance body engaging in the occlusal and gingival ends of said bracket body opening.

3. The appliance defined in claim 2, wherein said appliance body means for detachably securing the appliance to the bracket further includes shoulders at the gingival end of the appliance body engaging the lingual surfaces of the mesial and distal walls of the bracket body.

4. The appliance defined in claim 1, wherein said appliance body archwire retaining means includes a lingually opening mesiodistally extending slot having an occlusogingival depth substantially greater than the cross section of the archwire.

5. The appliance defined in claim 1, wherein said appliance body archwire retaining means includes a lingually opening mesiodistally extending slot having an occlusogingival depth substantially equal to the cross section of the archwire.

6. The appliance defined in claim 1, wherein said appliance body means for detachably securing the appliance to the bracket includes detent means at the occlusal end of the appliance body engaging the occlusal end of the bracket body opening and shoulders at the gingival end of the appliance body engaging the lingual surfaces of the mesial and distal walls of the bracket body, and an opening in the appliance at the gingival end aligning with the bracket body opening for permitting the mounting of auxiliaries.

7. The appliance defined in claim 1, wherein said appliance body means for detachably securing the appliance to the bracket includes detent means for engaging the bracket body.

8. The appliance defined in claim 7, wherein opening means is provided in the appliance body means to allow the insertion of a pin or other auxiliary in the occlusogingivally extending opening.

9. The appliance defined in claim 7, wherein the detent means is arranged to engage the mesial and distal sides of the bracket body.

10. The appliance defined in claim 1, wherein the plastic material is tooth colored.

11. An orthodontic appliance for use in combination with a metal bracket having attaching flanges, and a body extending labially from the flanges and having socket means at the occlusal and gingival ends thereof and a mesiodistally extending archwire slot opening along the occlusogingival axis of the body, said appliance comprising a body of plastic material having on the lingual side means for engaging said socket means and detachably locking the body to the bracket and means for coacting with the archwire slot to retain an archwire therein, said appliance body being sized to cover the bracket such that substantially none of the bracket is visible from the labial side, and said material being sufficiently resilient to flex and permit mounting and demounting of the appliance on the bracket.

12. The appliance defined in claim 11, wherein said means for engaging said socket means includes opposed detent portions which are spread apart when the appliance is snapped onto the bracket.

13. The appliance defined in claim 12, wherein said opposed detent portions include camming surfaces to facilitate spreading thereof and mounting on the bracket.

14. The appliance defined in claim 13, wherein said appliance body archwire retaining means includes a lingually opening mesiodistally extending slot.

15. An orthodontic appliance for use in combination with a metal bracket having a body with an occlusogingivally extending opening, attaching flanges at the lingual side of the body, and a mesiodistally extending archwire slot opening along the occlusogingival axis of the body, said appliance comprising a molded body of tooth colored plastic material, said appliance body having means for detachably locking the appliance to the bracket and means for coacting with the archwire slot to retain an archwire therein, and said appliance body being solid and of a size to cover the bracket so that substantially no portion of the bracket is visible from the labial side.

16. The appliance defined in claims 1, 11 or 15, wherein the appliance body archwire retaining means includes a lingually opening mesiodistally extending slot formed to snugly receive a round archwire.

17. The appliance defined in claims 1, 11 or 15, wherein the appliance body archwire retaining means includes a lingually opening mesiodistally extending slot formed to snugly receive a flat-sided archwire.

18. An orthodontic appliance for use in combination with a metal bracket having a body with an occlusogingivally extending opening, attaching flanges at the lingual side of the body, and a mesiodistally extending archwire slot opening gingivally at the gingivolingual corner of the body, said appliance comprising a body of plastic material capable of flexing for mounting same on a bracket, said body having means coacting with the bracket body for detachably securing the appliance to the bracket and having means to cover the labial surfaces of the bracket body and flanges and the mesial and distal surfaces of the bracket body so that substantially all of said surfaces are not visible from the labial.

* * * * *